United States Patent [19]

Sugano et al.

[11] 3,953,482

[45] Apr. 27, 1976

[54] PROCESS FOR PRODUCING QUINONES
[75] Inventors: Junichiro Sugano; Yasuhisa Kuriyama; Yukio Ishiuchi; Yoshitugu Minamikawa, all of Yokkaichi, Japan
[73] Assignee: Mitsubishi Gas Chemical Company, Inc., Tokyo, Japan
[22] Filed: Aug. 9, 1973
[21] Appl. No.: 387,229

[30] Foreign Application Priority Data
Aug. 16, 1972  Japan............................. 47-81472

[52] U.S. Cl............................. 260/396 R; 260/385
[51] Int. Cl.²................... C07C 49/66; C07C 49/68
[58] Field of Search...................... 260/385, 396 R

[56] References Cited
UNITED STATES PATENTS
2,373,003   4/1945   Arnold............................. 260/396
2,395,638   2/1946   Milas............................... 260/396

OTHER PUBLICATIONS
Arnold et al., Journal of Organic Chemistry, Vol. 5, pp. 250–252 (1940).
Charrier et al., Chemical Abstracts, Vol. 22, pp. 768 & 769 (1928).
Solyanikov et al., Chemical Abstracts, Vol. 70, 118553f (1969).
Hatcher et al., Chemical Abstracts, Vol. 18, p. 931 (1924).
Milas, Journal of the American Chemical Society, Vol. 59, pp. 2342–2344 (1937).
Oda et al., Chemical Abstracts, Vol. 54, 16369h (1960).
Tsutsumi, Chemical Abstracts, Vol. 54, 21543g (1960).

*Primary Examiner*—Vivian Garner
*Attorney, Agent, or Firm*—Sughrue, Rothwell, Mion, Zinn & Macpeak

[57]   ABSTRACT

A process for producing quinones corresponding to anthracenes or alkylnaphthalenes in high yields and selectivities, which comprises reacting the anthracenes or alkylnaphthalenes with hydrogen peroxide in the liquid phase in the presence of hydrogen chloride as a catalyst. Methanol, for example, may be used as a reaction medium.

13 Claims, No Drawings

PROCESS FOR PRODUCING QUINONES

BACKGROUND OF THE INVENTION

1. Field of the Invention

This invention relates to a process for producing quinones. More specifically, it relates to a process for producing quinones corresponding to the anthracenes or alkylnaphthalenes used as starting materials which comprises reacting the anthracenes of alkylnaphthalenes with hydrogen peroxide.

2. Description of the Prior Art

Quinones are important substances as industrial chemicals. Unsubstituted quinones are used as raw materials for dyes, and alkyl-substituted quinones are useful as raw materials for dyes or as media in the production of hydrogen peroxide.

One conventional method for producing anthraquinones comprises reacting anthracenes with hydrogen peroxide in acetic acid. If it is attempted to increase the conversion of the anthracenes in this method in the absence of a catalyst or in the presence of a sulfuric acid catalyst, their selectivity to the anthraquinones is reduced. On the other hand, if an attempt is made to increase the selectivity to anthraquinones, the conversion of the anthracenes becomes lower. In either case, the yeilds of the anthraquinones based on the anthracenes are low. Furthermore, the present inventors found that when this method was applied to the production of alkyl-substituted quinones from alkyl-substituted anthracenes or alkyl-substituted naphthalenes, the yield was very low, and the range of application was limited.

On the other hand, when cerous carbonate was used as a catalyst in the above-described method, the yield was as high as 82%. But since the catalyst is expensive, this method is not advantageous from a practical standpoint.

Another conventional method involves reacting anthracenes with hydrogen peroxide in tertiary-butyl alcohol using osmium tetroxide as a catalyst. However, this method is also not feasible because of the high cost of the catalyst.

It is an object of this invention to provide a process for producing quinones, which has a wide range of application and is commercially very advantageous, and which can give quinones in good yields based on anthracenes or alkylnaphthalenes (to be referred to simply as yields) by a very simple step using an inexpensive and readily available catalyst, while maintaining good conversions of the anthracenes or alkylnaphthalenes (to be referred to simply as conversions) and good selectivities to quinones (to be referred to simply as selectivities).

SUMMARY OF THE INVENTION

According to this invention, there is provided a process for producing quinones corresponding to the anthracenes or alkylnapththalenes used as starting materials which comprises reacting an anthracene or an alkylnaphthalene with hydrogen peroxide in the liquid phase in the presence of hydrogen chloride.

DETAILED DESCRIPTION OF THE INVENTION

The terms "anthracene" and "alkylnaphthalene" as used herein are intended to cover both anthracene per se and the alkyl-substituted derivatives thereof and the alkyl-substituted naphthalene derivatives, respectively as described hereinafter.

The anthracenes used in this invention are anthracene or anthracenes substituted by 1 to 8, preferably 1 to 3, alkyl groups at positions other than the 9- and 10-positions. The alkyl groups include both straight and branched chain groups containing not more than 10 carbon atoms, preferably not more than 6 carbon atoms, for example, methyl, ethyl, propyl, butyl and amyl. From these anthracenes, the corresponding anthraquinones containing oxygen atoms at the 9- and 10-positions are obtained. For example, 9, 10-anthraquinone is obtained from anthracene, and 2-methyl-9,10-anthraquinone is obtained from 2-methylanthracene.

The alkylnaphthalene used in this invention are alkylnaphthalenes substituted by an alkyl group only at the 2-position, or alkylnaphthalenes substituted by alkyl groups not only at the 2-position but also at the 3-, 5-, 6-, 7- and/or 8-positions. The alkyl groups of the substituted naphthalenes are the same as those of the anthracenes. The number of the alkyl groups in the alkylnaphthalenes is not more than 6, preferably not more than 3. From these alkylnaphthalenes, the corresponding naphthoquinones containing oxygen atoms at the 1- and 4-positions are obtained. For example, 2-methyl-1,4-naphthoquinone is obtained from 2-methylnaphthalene, and 2,3-dimethyl-1,4-naphthoquinone is obtained from 2,3-dimethylnaphthalene. This is schematically shown as follows:

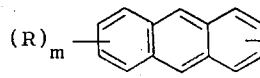 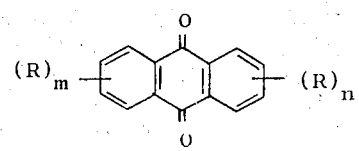

wherein R is an alkyl group having from 1 to 10 carbon atoms and $n$ and $m$ are each an integer from 0 to 4 and the sum of $n + m$ is 0 to 8, preferably up to 3.

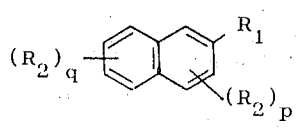 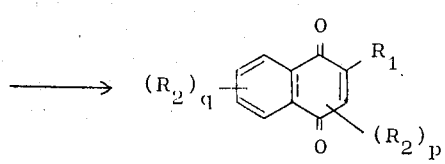

wherein $R_1$ and $R_2$ are each an alkyl group having 1 to 10 carbon atoms and $p$ is an integer of 0 to 1 and $q$ is an integer of 0 to 4 and the sum of $p + q$ is 0 to 5, perferably up to 3.

In the present invention, hydrogen chloride is used as a catalyst. The amount of hydrogen chloride used is 5 to 35 mols, preferably 10 mols, per mol of the anthracene or alkylnaphthalene used. The hydrogen chloride can be used as gas or as a solution in water or an organic solvent such as methanol.

As the hydrogen peroxide source not only can hydrogen peroxide per se be used but also any substance which liberates hydrogen peroxide under the reaction conditions, such as addition compounds of hydrogen peroxide, e.g., urea hydroperoxide ($H_2O_2 \cdot H_2NCONH_2$), $NaBO_2 \cdot H_2O_2 \cdot 3H_2O$ and $Na_2SiO_2 \cdot H_2O_2 \cdot H_2O$ can be used. The amount of hydrogen peroxide to be used is not particularly limited, but is generally 2 to 5 mols, more preferably 3 mols, per mol of the anthracene or alkylnaphthalene employed. Hydrogen peroxide may be added as such or as an aqueous solution of the hydrogen peroxide or the hydrogen peroxide source material. Hydrogen peroxide is preferred as the source material from a cost standpoint.

In the reaction of this invention, the presence of water adversely affects the reaction, and reduces the yield of quinones. Accordingly, it is necessary that the amount of water present in the reaction mixture before reaction be not more than 25% by weight, preferably not more than 10% by weight. From this viewpoint, when hydrogen chloride is used in the form of an aqueous solution, it should preferably be concentrated (at least 35%) hydrochloric acid. Where hydrogen peroxide is added in the form of its aqueous solution, an aqueous solution of the hydrogen peroxide having a concentration of at least 30% is preferred in commercial operation. On the other hand, the addition compounds of hydrogen peroxide can generally be used in a solid form.

The reaction is carried out in the liquid phase at autogeneous pressure. However, increased pressure can be employed where desired. In order to form this liquid phase, an aliphatic alcohol is used as a reaction medium. In order to obtain quinones in high yields, the use of saturated aliphatic alcohols having 1 to 5 carbon atoms, such as methanol, ethanol and isopropanol, is especially preferred among the aliphatic alcohols. The amount of the alcohol to be used is 30 to 300 ml, preferably 35 to 100 ml, per gram of the anthracenes or alkylnaphthalenes. If the amount is less than 30 ml, a large amount of power is required for stirring the reaction mixture, and if it is in excess of 300 ml, the reaction mixture becomes dilute and the rate of reaction is decreased. Accordingly, long periods of time are required to remove the reaction medium after completion of the reaction. In either case, the process is disadvantageous.

The reaction temperature used is 0° to 100°C, preferably 40° to 80°C. Where the reaction temperature is lower than 0°C, the rate of reaction is slow, and when it exceeds 100°C, decomposition of hydrogen peroxide occurs vigorously, and hydrogen peroxide is wasted. Thus, in either case, the process is not feasible.

By performing the reaction for 30 minutes to 2 hours under the above-described reaction conditions, the corresponding quinones can be obtained in high yields and high selectivities.

In order to recover the quinones from the reaction product mixture, the reaction medium, hydrogen chloride and water are first removed by distillation, and then the quinones are recovered by distillation at around 200° to 300°C and at reduced pressure to prevent decomposition.

The present invention has made it possible to produce anthraquinones from anthracenes in high yields and high selectivities by an extremely simple step using an inexpensive and readily available catalyst, and also to produce the corresponding quinones from alkyl-substituted anthracenes or alkyl-substituted naphthalenes in high yields and high selectivities. Since the catalyst and reaction medium used in this invention can be easily recovered, the process of the invention is extremely suitable from the standpoint of eliminating environmental pollution or public hazards as well as economical operation since such can be reused.

The following Examples are given to illustrate the present invention specifically, without intending to limit the invention thereby.

EXAMPLE

Each of the pulverized anthracenes or alkylnaphthalenes indicated in Table below was put into a four-necked flask. After adding each of the reaction media indicated in Table, with vigorous stirring hydrogen chloride (or hydrochloric acid) was added, and further, hydrogen peroxide was added. With stirring, the mixture of starting materials was maintained at a predetermined temperature for a predetermined time as indicated in Table. The reaction product mixture obtained was distilled to remove the reaction medium, hydrogen chloride, hydrogen peroxide and water, and subsequent vacuum distilled to afford each of the quinones indicated in Table. The reaction conditions used and results obtained are shown in Table. In the Table, the anthraquinone and alkylnaphthoquinone products listed are the 9,10-anthraquinones and the 1,4-naphthoquinones, respectively.

| Runs Nos. | 1 | 2 | 3 |
|---|---|---|---|
| Anthracenes or Naphthalenes | Anthracene | 2-Methyl Anthracene | 2-Amyl anthracene |
| Amount (g) | 0.9 | 1.0 | 1.0 |
| Form of Hydrogen Peroxide | 60 wt% Aqueous Solution | 60 wt% Aqueous Solution | 60 wt% Aqueous Solution |
| Amount as $H_2O_2$ (g) | 0.5 | 0.5 | 0.5 |
| Reaction Medium | Methanol | Ethanol | Methanol |
| Amount (ml) | 50 | 40 | 70 |
| Form of Hydrogen Chloride | 35% Hydrochloric Acid | 35% Hydrochloric Acid | 35% Hydrochloric Acid |
| Amount as HCl (g) | 1.8 | 1.8 | 1.9 |
| Amount of Water in Reaction Mixture before Reaction (g) | 3.7 | 3.7 | 3.8 |
| Reaction Temperature (°C) | 60 | 50 | 70 |
| Reaction Time (min.) | 60 | 60 | 45 |
| Reaction Product | Anthraquinone | 2-Methyl Anthraquinone | 2-Amyl Anthraquinone |
| Conversion* (mol%) | 98 | 90 | 94 |
| Selectivity (mol%) | 97 | 60 | 97 |
| Runs Nos. | 4 | 5 | 6 |
| Anthracenes or Naphthalenes | 2-Methyl-6-Amyl Anthracene | Anthracene | 2-Ethyl Anthracene |
| Amount (g) | 1.0 | 0.9 | 1.0 |
| Form of Hydrogen Peroxide | 31.2 wt.% Aqueous Solution | 90 wt.% Aqueous Solution | 60 wt.% Aqueous Solution |
| Amount as $H_2O_2$ (g) | 0.6 | 0.4 | 0.5 |

-continued

| Reaction Medium | Methanol | Methanol | Methanol |
|---|---|---|---|
| Amount (ml) | 50 | 200 | 100 |
| Form of Hydrogen Chloride | 14.7% Hydrochloric Acid | 35% Hydrochloric Acid | 35% Hydrochloric Acid |
| Amount as HCl (g) | 1.5 | 6.0 | 3.0 |
| Amount of Water in Reaction Mixture before Reaction (g) | 10.0 | 11.1 | 5.9 |
| Reaction Temperature (°C) | 60 | 40 | 90 |
| Reaction Time (min.) | 100 | 80 | 30 |
| Reaction Product | 2-Methyl-6-Amyl-Anthraquinone | Anthraquinone | 2-Ethyl-Anthraquinone |
| Conversion* (mol%) | 65 | 75 | 80 |
| Selectivity (mol%) | 92 | 96 | 90 |

| Runs Nos. | 7 | 8 | 9 |
|---|---|---|---|
| Anthracenes or Naphthlenes | 2-Butyl Anthracene | 2-Methyl Naphthalene | 2,3-Dimethyl Naphthalene |
| Amount (g) | 1.0 | 1.0 | 1.0 |
| Form of Hydrogen Peroxide | 60 wt.% Aqueous Solution | 60 wt.% Aqueous Solution | Urea Hydro-Peroxide |
| Amount as H₂O₂ (g) | 0.5 | 1.2 | 0.5 |
| Reaction Medium | Isopropanol | Methanol | Ethanol |
| Amount (ml) | 50 | 50 | 30 |
| Form of Hydrogen Chloride | Hydrogen Chloride Gas | Hydrogen Chloride Gas | Hydrogen Chloride Gas |
| Amount as HCl (g) | 1.5 | 4.5 | 1.5 |
| Amount of Water in Reaction Mixture before Reaction (g) | 0.3 | 0.8 | 0 |
| Reaction Temperature (°C) | 80 | 30 | 70 |
| Reaction Time (min.) | 20 | 60 | 60 |
| Reaction Product | 2-Butyl-Anthraquinone | 2-Methyl-Naphthoquinone | 2,3-Dimethyl-Naphthoquinone |
| Conversion* (mol%) | 90 | 80 | 70 |
| Selectivity (mol%) | 70 | 75 | 79 |

*Not corrected based on the molar ratio of hydrogen peroxide to the anthracenes or alkylnaphthalenes.

COMPARATIVE EXAMPLE

A 100 ml three-necked flask was charged with 1.0 g of amylanthracene, 50 ml of dichloromethane, and an equilibrium peracetic acid-acetic acid aqueous solution (consisting of 41.0% by weight of peracetic acid, 17.4% by weight of hydrogen peroxide, 29.8% by weight of acetic acid, 1.0% by weight of sulfuric acid and 9.9% by weight of water) in an amount corresponding, as amount of active oxygen, to 3 molar times the amylanthracene, and with occasional shaking, allowed to stand for 2 days at 25°C. The resulting reaction product mixture was washed with a 5% by weight aqueous solution of sodium hydroxide to remove the acetic acid, peractetic acid and hydrogen peroxide, and then dried. Dichloromethane was removed by vacuum distillation, and the resulting crude amylanthraquinone was gas-chromatographically analyzed. The conversion was 75%, and the selectivity was 32%.

While the invention has been described in detail and with reference to specific embodiments thereof, it will be apparent to one skilled in the art that various changes and modifications can be made therein without departing from the spirit and scope thereof.

What is claimed is:

1. A process for producing anthraquinones or alkyl-substituted naphthoquinones, which comprises reacting in the liquid phase at a temperature of from 0° to 100°C an anthracene or an alkylnaphthalene with hydrogen peroxide in the presence of 5–35 moles of hydrogen chloride per mole of the anthracene or alkylnaphthalene, the total amount of water in said reaction mixture before reaction being not more than 25% by weight based on the total weight of the reaction mixture;
   wherein said anthracene is anthracene or an anthracene substituted by 1 to 8 alkyl groups each of which contains not more than 10 carbon atoms at positions other than the 9- and 10-positions of said anthracene; and
   wherein said alkylnaphthalene is an alkylnaphthalene substituted by an alkyl group which contains not more than 10 carbon atoms only at the 2-position, or an alkylnaphthalene substituted by alkyl groups, each of which contains not more than 10 carbon atoms, in the 2-position and in at least one of the 3-, 5-, 6-, 7- or 8-positions.

2. The process of claim 1, wherein the amount of hydrogen chloride is 10 mols per mol of the anthracene or alkylnaphthalene.

3. The process of claim 1, wherein the reaction is at a temperature of from 40° to 80°C.

4. The process of claim 1, wherein said reaction is in an aliphatic alcohol as a reaction medium.

5. The process of claim 4, wherein said alcohol is a saturated aliphatic alcohol containing 1 to 5 carbon atoms.

6. The process of claim 5, wherein said alcohol is methanol, ethanol or isopropanol.

7. The process of claim 4, wherein the amount of the alcohol ranges from 30 to 300 ml per gram of the anthracene or alkylnapththalene.

8. The process of claim 7, wherein the amount of the alcohol ranges from 35 to 100 ml per gram of the anthracene or alkylnaphthalene.

9. The process of claim 7 wherein the amount of hydrogen peroxide ranges from 2 to 5 moles per mole of the anthracene or alkylnaphthalene.

10. The process of claim 1, wherein the amount of hydrogen peroxide ranges from 2 to 5 mols per mol of the anthracene or alkylnaphthalene.

11. The process of claim 10, wherein the amount of hydrogen peroxide is 3 mols per mol of the anthracene or alkylnaphthalene.

12. The process of claim 1 wherein said alkylnaphthalene is reacted and said alkylnaphthalene is substituted only at the 2-position with an alkyl group having not more than 10 carbon atoms.

13. The process of claim 1 wherein the reaction is conducted for 30 minutes to 2 hours.

* * * * *